United States Patent [19]

Issa

[11] Patent Number: 5,658,280

[45] Date of Patent: Aug. 19, 1997

[54] RESECTOSCOPE ELECTRODE ASSEMBLY WITH SIMULTANEOUS CUTTING AND COAGULATION

[76] Inventor: Muta M. Issa, 2479 Alameda de las Pulgas, Redwood City, Calif. 94061

[21] Appl. No.: 445,597

[22] Filed: May 22, 1995

[51] Int. Cl.$^6$ ..................................................... A61B 17/39
[52] U.S. Cl. .................. 606/46; 606/45; 606/41; 606/48; 606/49
[58] Field of Search .............................. 606/37–42, 45–50

[56] References Cited

U.S. PATENT DOCUMENTS

| | | |
|---|---|---|
| 3,850,162 | 11/1974 | Iglesias . |
| 3,850,175 | 11/1974 | Iglesias .................................. 606/46 |
| 4,060,087 | 11/1977 | Hiltebrandt et al. ..................... 606/48 |
| 4,116,198 | 9/1978 | Roos ...................................... 606/46 |
| 4,917,082 | 4/1990 | Grossi et al. ........................... 606/46 |
| 4,969,885 | 11/1990 | Farin . |
| 5,190,541 | 3/1993 | Abele et al. ............................ 606/46 |
| 5,192,280 | 3/1993 | Parins .................................... 606/50 |
| 5,196,011 | 3/1993 | Korth et al. ............................ 606/46 |
| 5,267,998 | 12/1993 | Hagen ..................................... 606/46 |
| 5,330,471 | 7/1994 | Eggers . |

OTHER PUBLICATIONS

Mebust, "Transurethral Prostatectomy", *Urologic Clinics of North America*, vol. 17, No. 3, pp. 575–585, Aug. 1990.

*Primary Examiner*—Lee S. Cohen
*Assistant Examiner*—Michael Peffley
*Attorney, Agent, or Firm*—Wilson Sonsini Goodrich & Rosati

[57] ABSTRACT

An electrode assembly for a resectoscope includes, a cutting electrode with a loop distal tip and a coagulation electrode with a loop distal tip. A support frame connects the cutting and coagulation electrodes to an energy source which supplies energy from the energy source to the electrodes. The coagulation electrode provides tissue coagulation simultaneously while the cutting electrode cuts tissue. A resectoscope is disclosed which includes the electrode assembly. The resectoscope includes a sheath with a sheath lumen, a working element, and a visualization apparatus.

20 Claims, 6 Drawing Sheets

RESECTOSCOPE ELECTRODE ASSEMBLY WITH SIMULTANEOUS CUTTING AND COAGULATION

BACKGROUND OF THE INVENTION

1. Field of the Invention

This invention relates generally to resectoscope electrodes, and more particularly, to a resectoscope electrode assembly that simultaneously cuts and coagulates.

2. Description of Related Art

BPH is a benign overgrowth of the prostate gland that is situated at the bladder outlet. BPH is one of the most common conditions affecting men over the age of 50. The incidence increases with age and reaches 80 to 90% at 80 years. In the majority of patients, the BPH causes no symptoms. However, in a certain percentage of patients, the BPH will slowly and progressively obstruct the urinary outflow causing voiding symptoms of bladder obstruction and irritation. Furthermore and yet in a smaller percentage, these symptoms progress to cause complete urinary retention, urinary infections, bladder stones, and kidney damage. The decision to treat or not to treat patients is governed by the presence and absence of symptoms and their severity. Therefore, in the far majority of BPH patients (approximately 70%) who remain asymptomatic, no treatment is needed. In the symptomatic BPH patients, a wide variety of treatment strategies are available.

There are two groups of surgical therapies for BPH based according to the anesthesia requirement. The first group requires general or spinal anesthesia and includes open prostatectomy, transurethral resection of the prostate (TURP), transurethral incision oft he prostate (TUIP), transurethral vaporization of the prostate (TVP), visual laser assisted prostatectomy (V-LAP), contact laser prostatectomy, prostate balloon dilation, and intra-prostatic stents. TURP is the "gold standard" treatment. It has been the most efficacious and durable of all the surgical treatments, with a success rate of 80-90%.

Figure 1:
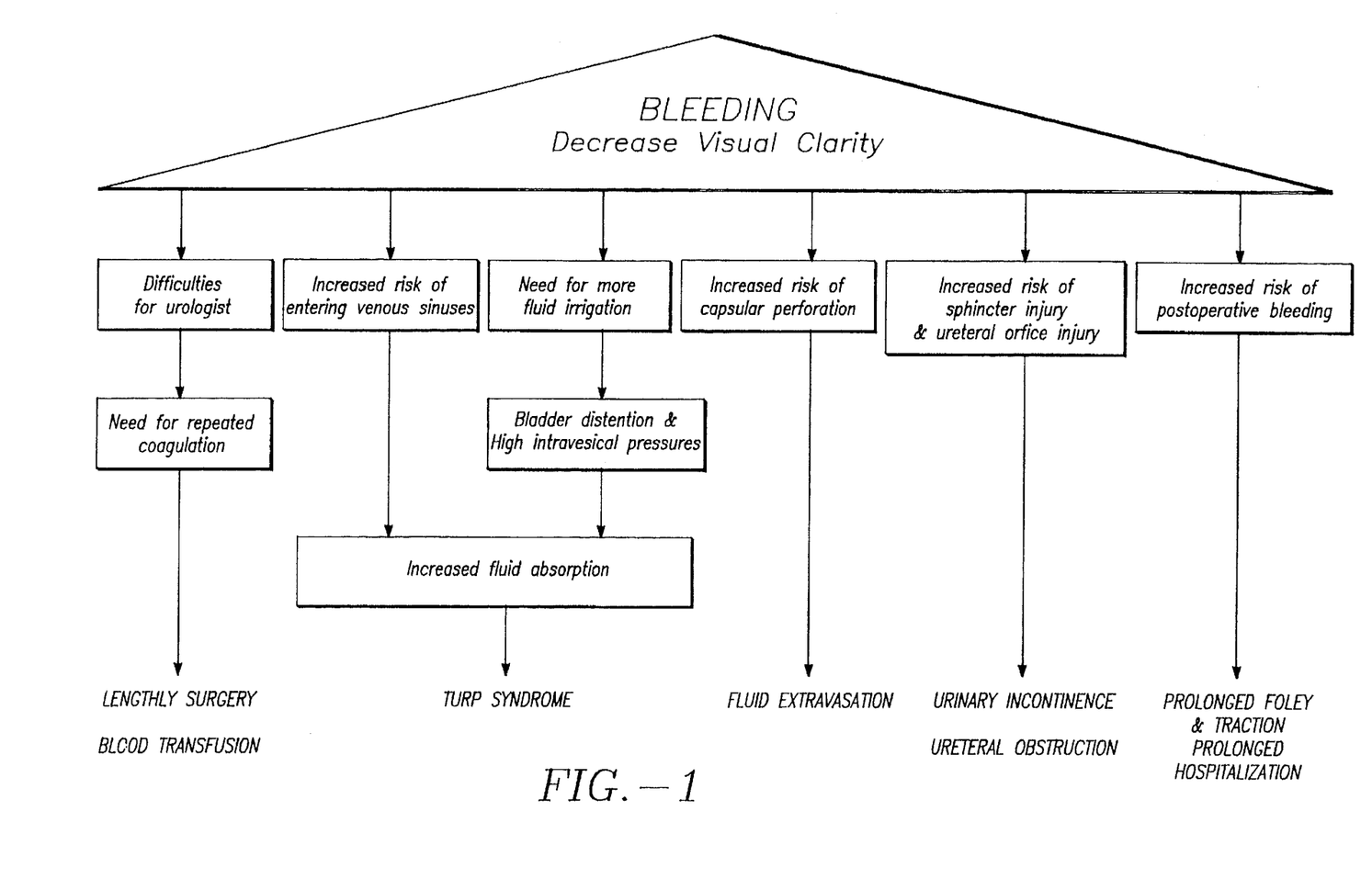
FIG. 1 is a flow diagram illustrating the complications of the standard TURP procedure.

The prostate is a highly vascular organ which bleeds during resection (TURP). Bleeding causes a decrease in visual clarity which in turn leads to a variety of intraoperative difficulties with undesirable consequences. The bleeding is the main offending factor responsible for the majority of the problems. FIG. 1 is a flow chart listing the complications of the standard TURP.

A typical resectoscope for transurethral resection consists of four main elements. The first element is a rigid telescope for observing the interior of the urinary tract where the surgical procedure is performed. The telescope comprises an objective lens and a series of relay lenses housed within an endoscope barrel or stem, the stem being connected to an eyepiece housing containing suitable lenses for proper magnification. The second element takes the form of a handle assembly commonly referred to as a working element. The working element can serve as the means for connecting electrosurgical current from an electrosurgical generator to the third element, an electrode assembly. The working element is also capable of slidably the electrode assembly along the longitudinal axis of the resectoscope. The combination of the telescope, working element, and electrode assembly is locked into a fourth element, a resectoscope sheath. The sheath consists of a tube and a union body and lock assembly. In the operative procedure the entire resectoscope is placed into the urethra.

The usual resectoscope electrode assembly is in the form of a U-shaped tungsten wire loop, the ends go to one or more wires that fit in a socket in a working element of the resectoscope for current conduction. The wire arms usually merge at their proximal ends and are jointed to an electrode lead extending back to the working element of the instrument. To brace the cutting loop so that it remains uniformly spaced from the telescope stem, a metal spacing sleeve is commonly provided between the telescope stem and either parallel electrode arms or the distal portion of the electrode lead immediately adjacent to those arms. The metal spacing sleeve is slidable along the telescope stem as the electrode assembly is advanced and retracted and, because of the direct contact between the spacing sleeve and the telescope stem, it has been necessary in the part to insure adequate insulation between the electrode and the sleeve.

To date, all new and alternative surgical therapies have generally failed to exhibit similar efficacy and durability, however, they have shown certain advantages in minimizing morbidity, the mount of blood loss that is experienced and are easier to perform. There is a need for a safer and less morbid approach than TURP that exhibits similar durable efficacy.

The second group of surgical therapies require local anesthesia without the need for general or spinal anesthesia. These treatments utilize different energies to deliver thermal therapy to the prostate. They include transurethral microwave thermotherapy (TUMT), transurethral thermal-ablation therapy (T#), high intensity focused ultrasound (HIFU), laser delivered interstitial thermal therapy (LDIT), and transurethral needle ablation of the prostate (TUNA). These treatments are less morbid that conventional TURP. Such thermal therapies are currently under investigation and will require completion of phase three trials and FDA approval before they make their debut into the market.

There is a need for a bloodless TURP apparatus, as shown in FIG. 1, thus alleviating virtually all of the problems of the standard TURP devices. This can be achieved in a TURP apparatus which provides simultaneous cutting and coagulation.

SUMMARY OF THE INVENTION

Accordingly, it is an object of the invention is to provide an electrode assembly for a resectoscope that includes a coagulation electrode loop that operates simultaneously with a cutting electrode loop.

Another object of the invention is to provide an electrode assembly for a resectoscope that includes a coagulation electrode and a cutting electrode, each with a distal end loop configuration.

Still another object of the invention is to provide an electrode assembly for a resectoscope which includes separate cutting and coagulation loops which move under direct endoscopic vision.

A further object of the invention is to provide an electrode assembly for a resectoscope which includes separate cutting and coagulation electrodes which move in the same direction.

Another object of the invention is to provide an electrode system to improve TURP procedures that is substantially bloodless.

A further object of the invention is to provide an electrode system to improve TURP procedures that provides increased visual clarity.

Yet a further object of the invention is to provide a converter box for an electrode assembly suitable for a resectoscope.

These and other objects of the invention are provided in an electrode assembly for a resectoscope. The electrode assembly for a resectoscope includes, a cutting electrode with a loop distal tip and a coagulation electrode with a loop distal tip. A support frame connects the cutting and coagulation electrodes to an energy source which supplies energy from the energy source to the electrodes. The coagulation electrode provides tissue coagulation simultaneously while the cutting electrode cuts tissue.

In another embodiment of the invention, a resectoscope is disclosed which includes the electrode assembly. The resectoscope includes a sheath with a sheath lumen, a working element, and a visualization apparatus.

The resectoscope includes a sheath including a sheath lumen, a distal end and a proximal end. An electrode assembly includes, a cutting electrode with a distal end with a loop geometry, a coagulation electrode with a distal end, with the coagulation electrode distal tip coagulating tissue simultaneously when the cutting electrode cuts tissue. A handle assembly is attach to the proximal end of the sheath. Further, a visualization apparatus is provided and housed in a sheath lumen extending from the sheath distal end to a proximal end of the handle assembly.

The present invention provides an intra-operative electrode assembly for a resectoscope, and a resectoscope that provides: simultaneous cutting and coagulation under direct visualization; a performance that is easier for the urologist; a lower risk of entering venous sinus; a lower risk of further bleeding; decreased potential for blood transfusions; less fluid irrigation and bladder distention; less risk of TURP syndrome; lower risk of capsular penetration and subsequently less risk of fluid extravasation into the abdomen; lower risk of urinary sphincter injury and subsequently less risk of urinary incontinence; lower risk of ureteral orifice injury and subsequently less risk of ureteral obstruction and vesicoureteral reflux; shorter operative time; less need for bladder catheterization and Foley traction postoperatively; lower risk of postoperative scarring and bladder neck contracture; less need for postoperative bladder irrigation; a shorter duration for postoperative Foley catheterization. a shorter hospital stay; and an associated cost less than the standard TURP.

BRIEF DESCRIPTION OF THE FIGURES

FIG. 2 (a) is a perspective view of one embodiment of the electrode assembly of the present invention.

DETAILED DESCRIPTION

The present invention is an electrode assembly for a resectoscope includes, a cutting electrode with a loop distal tip and a coagulation electrode with a loop distal tip. A support frame connects the cutting and coagulation electrodes to an energy source which supplies energy from the energy source to the electrodes. The coagulation electrode provides tissue coagulation simultaneously while the cutting electrode cuts tissue. A resectoscope is disclosed which includes the electrode assembly. The resectoscope includes a sheath with a sheath lumen, a working element, and a visualization apparatus.

Further, as compared to devices currently used for standard TURP's, the present invention has: increased visual clarity; a performance that is easier for the urologist; a lower risk of entering venous sinus; a lower risk of further bleeding; decreased potential for blood transfusions; less fluid irrigation and bladder distention; less risk of TURP syndrome; lower risk of capsular penetration and subsequently less risk of fluid extravasation into the abdomen; lower risk of urinary sphincter injury and subsequently less risk of urinary incontinence; lower risk of ureteral orifice injury and subsequently less risk of ureteral obstruction and vesicoureteral reflux; shorter operative time; less need for bladder catheterization and Foley traction postoperatively; lower risk of postoperative scarring and bladder neck contracture; less need for postoperative bladder irrigation; a shorter duration for postoperative Foley catheterization. a shorter hospital stay; and an associated cost less than the standard TURP.

For purposes of this disclosure, the word "simultaneous" means, (i) RF energy is supplied at the same time to the cutting and coagulation electrode distal tips, (ii) RF energy is supplied to both distal tips in less than 1 second, (iii) within the same hand action, e.g., on a forward stroke or on a back stroke, energy is only supplied in the cutting mode, and on the other stroke it is only supplied in the coagulation mode, (iv) when energy is delivered to the distal tips the coagulation tip has a thermal or RF spread of energy that reaches the cutting distal tip when it is cutting, (v) two currents go out to both distal tips at the same time and (vi) the transfer of thermal energy from the coagulation electrode to the site of the cutting electrode occurs in less than 1 millisecond. It will be appreciated that thermal spread from the coagulation tip is controllable. The higher the energy, the greater the spread. The lower the energy, the lower the spread. It is possible to have the RF energy spread extend beyond the cutting electrode's physical location.

The present invention can be operated in bipolar or monopolar modes. Bipolar is particularly suitable when the two electrodes are closer together, and in those instances when RF energy spread between the two electrodes is desired to be limited or controlled. The shorter the distance between the two electrodes, then RF energy spread does not appreciably extend beyond the electrodes. This is particularly useful in those instances where that RF energy spread to surrounding or adjacent tissues or structures is can lead to an undesirable result.

Further, the present invention is useful in a variety of applications including but not limited to urology, neurology, cardiology, as well as other surgical interventions.

Figure 2A:
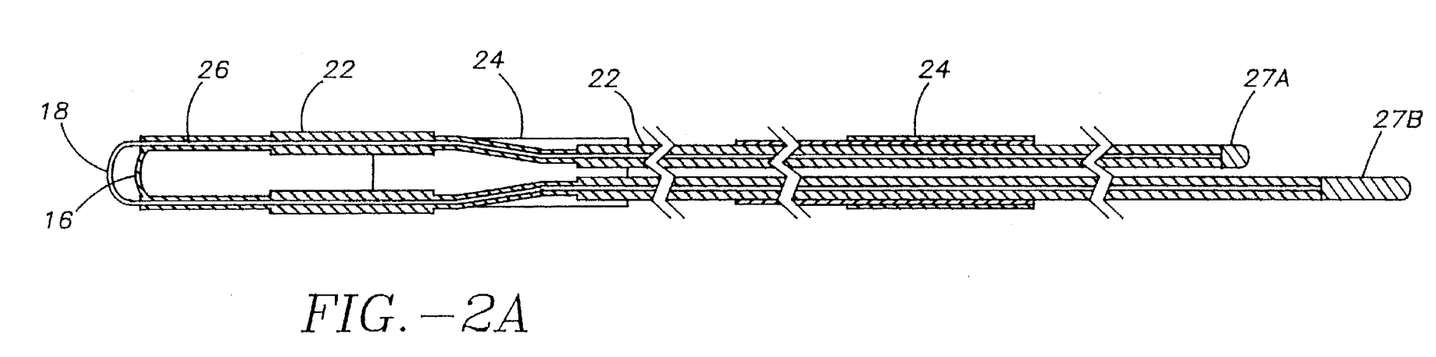
Figure 2B:
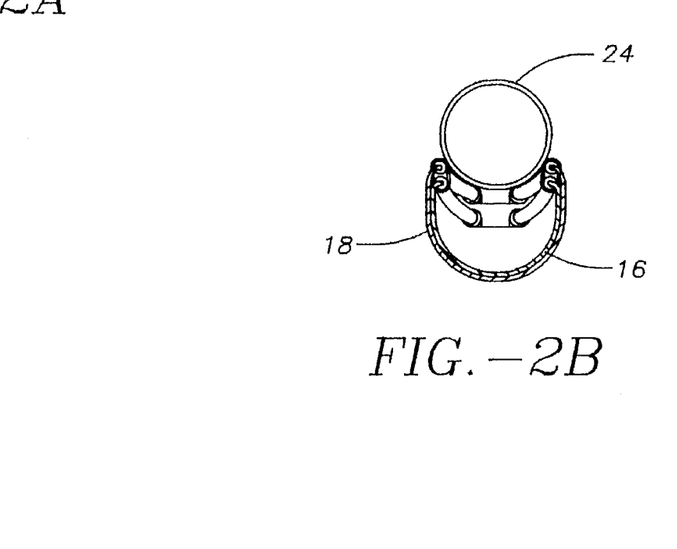
FIG. 2(b) is a cross-sectional view of the electrode assembly of FIG. 2(a) taken along the lines 2(b)—2(b).

Referring now to FIGS. 2 (a) and 2(b), electrode assembly 10 includes a cutting electrode 12, a coagulation electrode 14, both of which terminate at distal tips 16 and 18 respectively. Distal tips 16 and 18 preferably have a loop geometry. Suitable electrode loop geometries include but are not limited to, radial, circular, elliptical, curved, rounded, bowed, arc, arch, crescent, semicircle, malleable and roller (whirler, revolver, rotary) cylinder, and can also include a roller ball. In one embodiment, a plurality of roller balls are included to form a loop with any of the previously mentioned geometries. The loop size diameter can be 3 mm (9 French gauge) to 10 mm (30 French gauge), or any size that will fit in a commercially available resectoscope (22 to 28 French gauge). Cross-section shapes of wires include, circular, hemicircular, any portion of a circle, square, rectangular, triangular, shapes such as hexagon, octagon, etc, flat plate, and combinations of the above. The wire can include horizontal or longitudinal grooves. The cross-section diameter of the wire can be from about 0.25 to 4 mm. The size of the roller can be from 0.25 to 4 mm.

A support frame 20 connects cutting electrode 12 and coagulation electrode 14 to an energy supply source. Support frame 20 provides structural support. Preferably, support frame 20 is made of stainless or corrosion resistant material, and the like. Electrode assembly 10 can also include a stiffener sleeve(s) 22, an optical guide sleeve(s) 24, and an insulation sleeve 26. End caps 27(a) and 27(b) are included at a proximal end of electrode assembly 10. Stiffiner sleeve 22 extends along electrode assembly 10 to variable distances to permit sufficient wire rigidity. Optical guides 24 are mounted to stiffiner sleeves 22 anywhere along the length of electrode assembly 10 depending on the design of the resectoscope.

Cutting and coagulation electrode distal tips 16 and 18 can be made of a variety of electrical conductive materials including but not limited to tungsten, its alloys, stainless steel and the like. A preferred material is a tungsten wire. Insulating sleeve can be made of a dielectric material including but not limited to, (i) fluropolymers, (ii) polyimide, (iii) polyamide, (iv) polyaryl sulfone and (v) silicone plastic. The thickness of insulation sleeve is in the range of about 0.001 to 0.100 inches. Optic guide sleeve 24 is a guide tube for optics, including but not limited to relay lenses and the like, and guides and supports cutting electrode and coagulation distal tips 16 and 18 respectively. Optical guide sleeve 24 can be cylindrical, tubular, or a portion of a cylinder or tube. Further, optical guide sleeve 24 can be singular or multiple in number. It can range in length from 0.1 mm to 20 cm, i.e., it can extend from visualization apparatus to coagulation electrode distal tip 18.

Figures 3A, 3B:
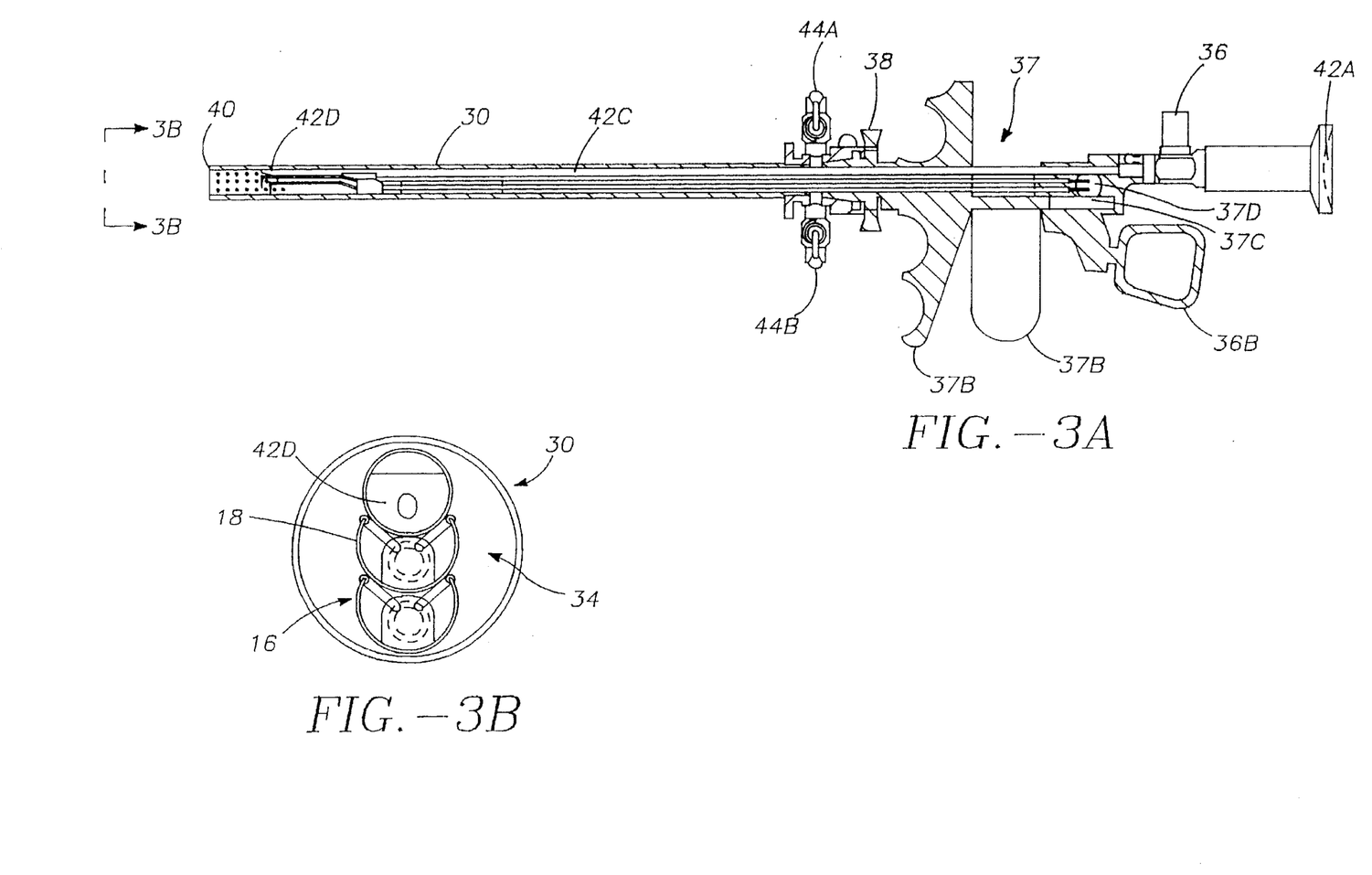
FIG. 3(a) is another perspective view of the electrode assembly of FIG. 2(a).
FIG. 3(b) is a cross-sectional view of the distal end of the resectoscope sheath.
Figure 4A:
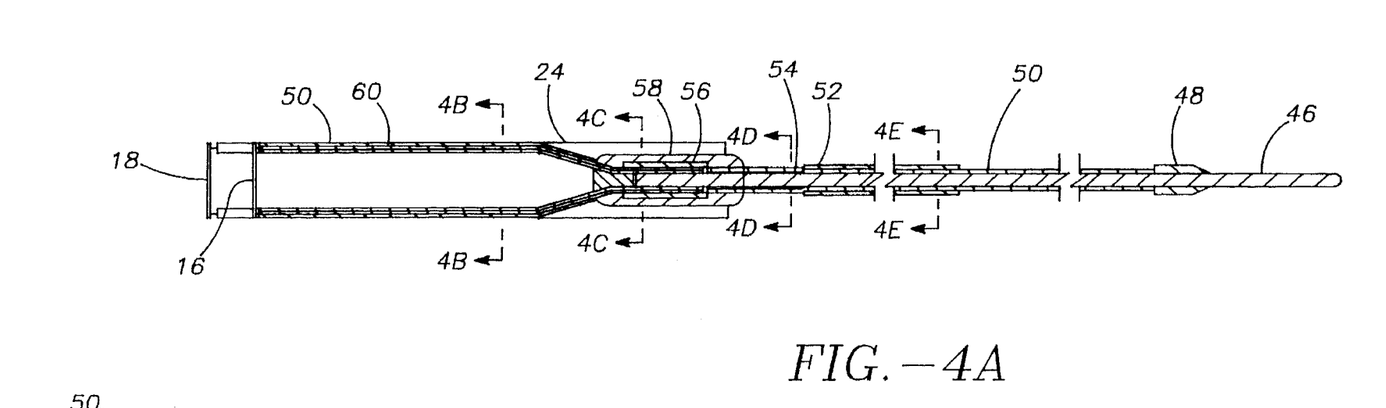
FIG. 4(a) is a perspective view of a second embodiment of the electrode assembly of the present invention.
Figure 4B:
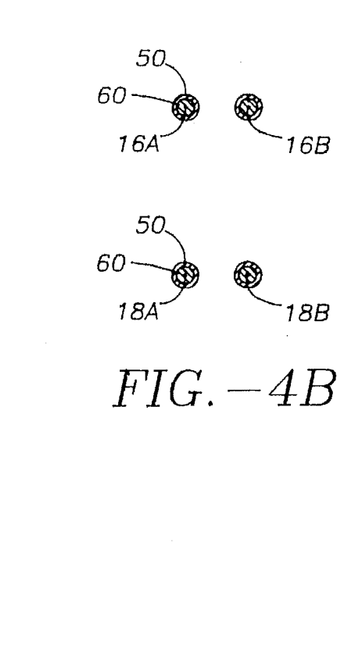
FIG. 4(b) is a cross-sectional view of the electrode assembly of FIG. 4(a) taken along the lines 4(b)—4(b).
Figures 4C, 4D:
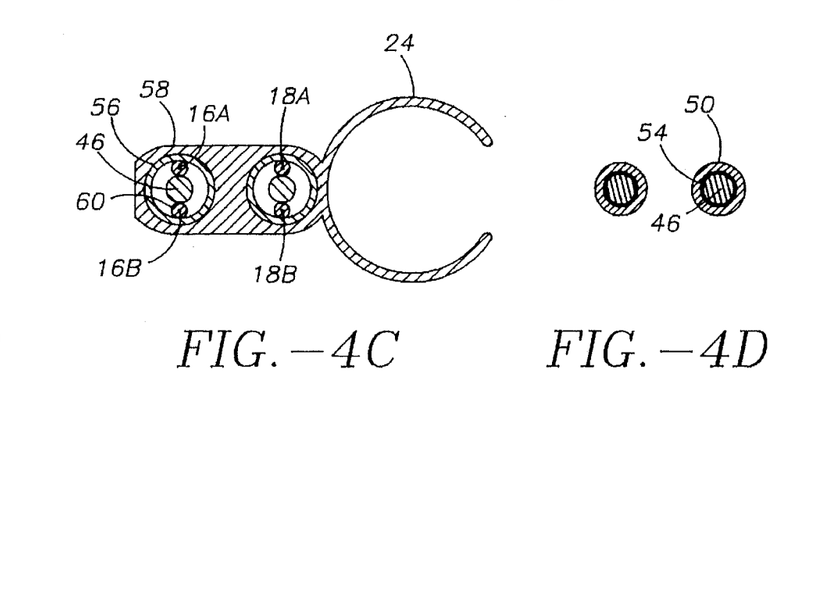
FIG. 4(c) is a cross-sectional view of the electrode assembly of FIG. 4(a) taken along the lines 4(c)—4(c).
FIG. 4(d) is a cross-sectional view of the electrode assembly of FIG. 4(a) taken along the lines 4(d)—4(d).
Figure 4E:
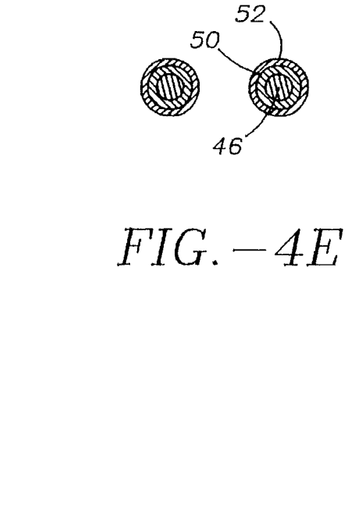
FIG. 4(e) is a cross-sectional view of the electrode assembly of FIG. 4(a) taken along the lines 4(e)—4(e).

As illustrated in FIG. 3(a), a resectoscope 28 has a sheath 30 with a sheath lumen 34 which extends substantially along the entire length of sheath 30. Electrode assembly 10 is positioned in sheath lumen 34. Resectoscope 28 includes a working element 37 which is attached to sheath 30. A visualization apparatus 42 fits into working element 37. Visualization apparatus 42 includes a proximal end 42(a) with an eyepiece, a socket 42(b) for attachment of a light source cable, a rod lens 42(c) and a distal end 42(d). Lens rod 42(c) is the actual body of visualization apparatus 42 and extends from proximal end 42(a) to distal end 42(d). Also included are an inflow socket 44(a) and an outflow socket 44(b).

Cutting electrode distal tip 16 is positioned closer to sheath proximal end 38 than coagulation electrode distal tip 18. Cutting electrode distal tip 16 and coagulation electrode distal tip 18 can be in a fixed relationship to each other, or a variable distance can be established between the two tips. Preferably, cutting electrode distal tip 16 and coagulation electrode distal tip 18 are separated by a distance of 5 mm or less, or 3 mm or less. This permits sufficient time for cutting electrode tip 16 to cut tissue, while simultaneously coagulation electrode 14 is coagulating tissue at a slight distance away. The proper separation permits the two tips from effectively cutting and coagulating simultaneously without interfering with each other.

Working element 37 of resectoscope 28 can include the following elements (i) a thumb grip handle 37(a), (ii) a finger grip handle 37(b), (iii) a spring mechanism 37(c) located between the two handles (this serves in maintaining the handles apart, i.e., the electrode assembly tips inside the sheath; further, spring mechanism 37(c) also self restores this position following manual deployment out of the electrode assembly tip), (iv) an internal socket 37(d) where the proximal end of the electrode assembly is plugged into and secured in for electric current connection and transmission, and (v) an external socket 37(e) for plugging in an external cable that transits electric currents from the converter and energy source. All connections are insulated to prevent dissipation of electric current. Cutting and coagulation electrodes 12 and 14 extend into handle assembly 37.

As shown in FIG. 3(b) optical guide sleeve 24, (i) guides the placement and attachment of rod lens to electrodes 12 and 14 and stabilizes the two together, (ii) maintains and supports the correct and proper position of electrode assembly 10 through sheath lumen 34 and (iii) allows electrode assembly 10 to longitudinally slide in and out parallel to the lens rod during usage and to maintain this positional relationship throughout the surgical procedure.

An alternative electrode assembly 10 is illustrated in FIGS. 4(a) through 4(e). In this embodiment, a single arm conductor rod 46 transfers and transmits two electrical currents through rods 46(a) and 46(b) to the body via cutting electrode distal tip which is divided into two wires 16(a) and 16(b), and coagulation electrode distal tip also divided into two wires 18(a) and 18(b). The energy delivery is simultaneous through cutting electrode distal tip 16 and coagulation electrode distal tip 18. The purpose of the single arm conductor rod is to allow its use in a variety of commercially available resectoscopes. Further includes is a lock catch 48, outer insulation 50, steel sleeve 52, inner insulation 54, crimp 56, housing 58, optic guide 24 and steel tubing 60.

Figure 5:
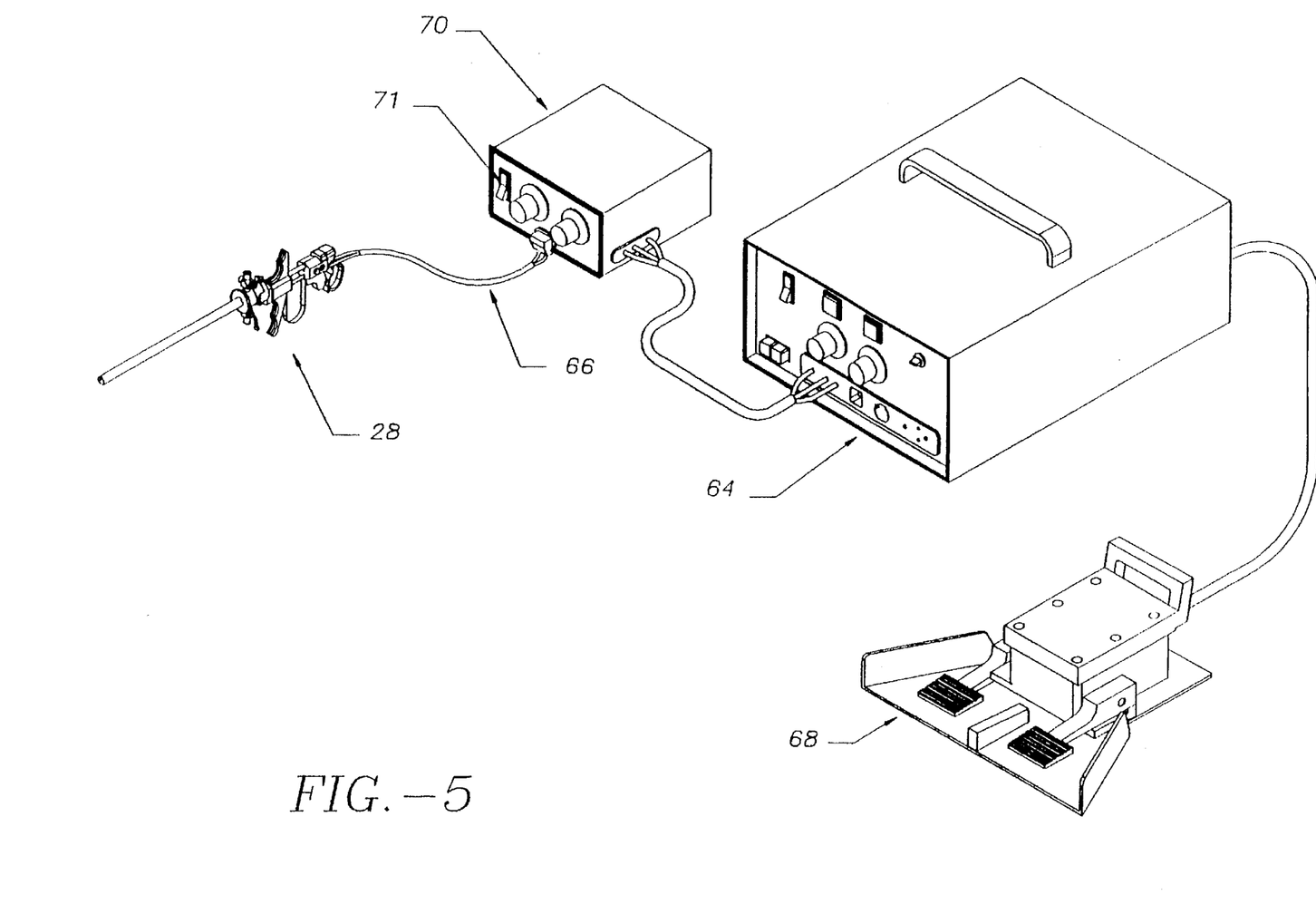
FIG. 5 is a schematic view of a the resectoscope, power supply and converter of the present invention.

Referring now to FIG. 5, resectoscope 28 is electrically coupled to a power supply 64 with an electrical conduit 66. The amount of energy delivered is activated by foot control 68. Suitable RF power supplies are commercially available from Valley Labs, Erbe, as well as from other commercial vendors.

A converter box 70 permits substantially any commercially available power supply to be utilized with the present invention. Power is provided by RF energy delivered to power supply 64. The amount of energy delivered is adjusted on a from panel 71 of converter box 70.

When the apparatus is operated using the handle controls 37(a) and 37b, the cut and coagulation modes are determined by the relative position of the associated control hobs. Each control setting is independent of the other. In a typical use, distal loop 18 coagulates, and proximal loop 16 cuts. Any control can be set to an "off" position where there is no RF power delivery to the corresponding loop. Proper association of the control knobs and the proximal and distal loops is ensured by a device connector.

The apparatus can also be operated with a foot pedal to activate the power supply. This in turn activates converter box 70. Three modes of currents are deliver: (i) cut and coagulate, (ii) cut and cut, and (iii) coagulate and coagulate. The three modes are controlled manually by a separate switch located either on the external cable near its entrance into the resectoscope instrument or at the converter box.

Figure 6:
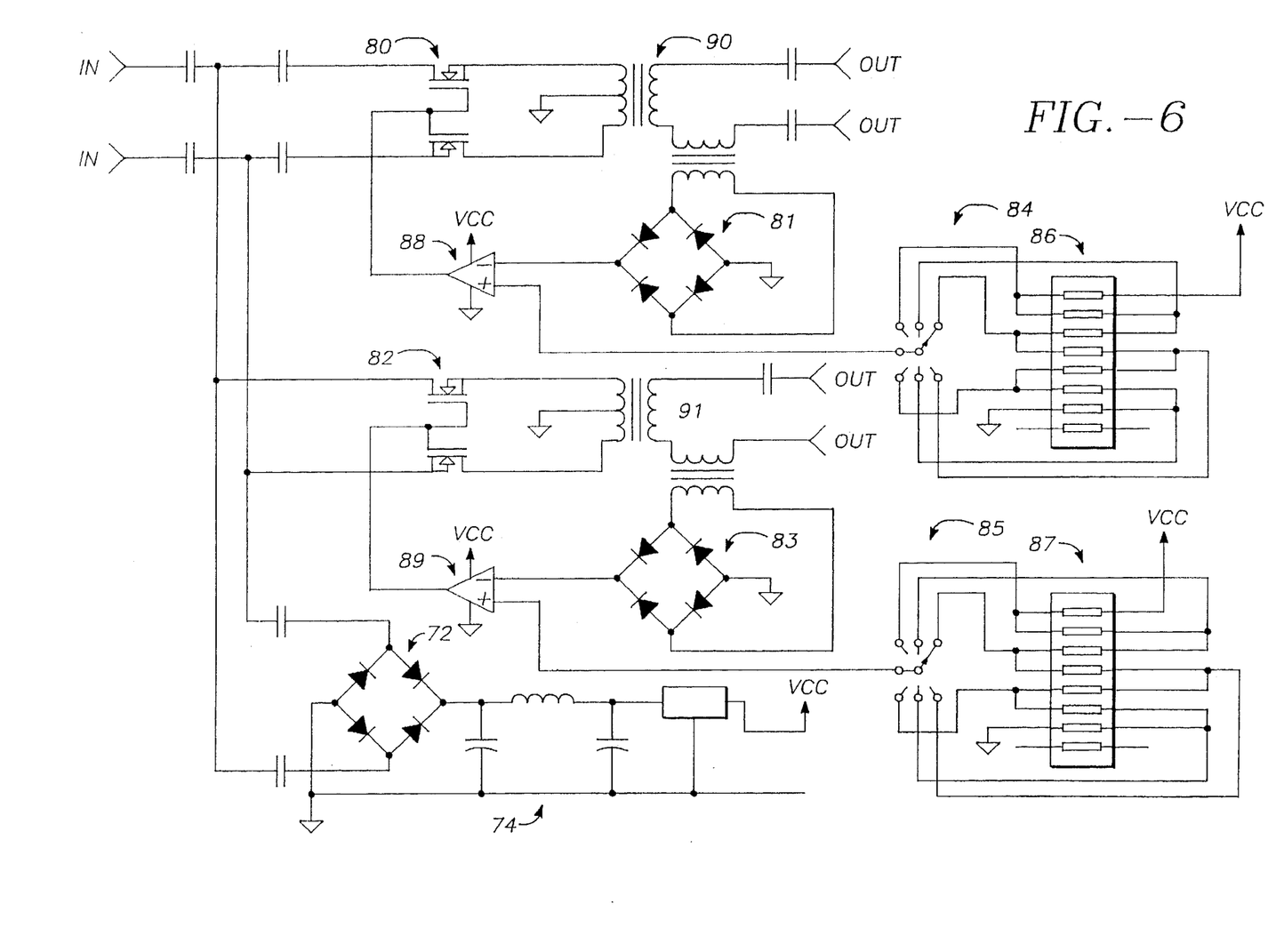
FIG. 6 is a schematic diagram of the electronics for a converter of the present invention.

As shown in FIG. 6 bridge 72 rectifies the RF signal, which is then filtered by filter 74, and regulated by a regulator which provides Vcc to the control electronics for two channels. The two control channels are identical. RF from an external generator is delivered symmetrically to first and second FET device pairs 80 and 82, which act as voltage controlled power resistors. A gate voltage is generated by sampling an output from current and a bridge rectifiers 81 and 83, and comparing it to a preset level. The preset level is obtained through six position switchs 84, 85 and resistor networks 86 and 87 connected to Vcc power supply as a divider. Amplifiers 88 and 89 compare the two levels and the difference drives FET pair gates 80 and 82. Output RF to cutting electrode distal tip 16 and coagulation electrode distal tip 18 is provided through isolation transformers 90 and 91 that also bias first and second FET pairs 80 and 82. Capacitors on the output provide DC blocking to further protect the patient.

In operation, power supply 64 is set to a power level greater than the maximum required level by at least 5 watts, in order to power the electronics. Individual power level for each channel is preset by control switches. When power supply 64 delivers power, each channel delivers an attenuated level of power according to the switch setting.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

I claim:

1. An electrode assembly for a resectoscope, comprising:
   a cutting electrode with a loop distal tip;
   a coagulation electrode with a loop distal tip in fixed physical relationship with the cutting electrode loop distal tip; and
   a support frame connected to the cutting and coagulation electrodes and adapted to be coupled to an energy source to split and supply energy from the energy source to both the cutting and coagulation electrodes, wherein the coagulation electrode provides tissue coagulation simultaneously while the cutting electrode cuts tissue.

2. The electrode assembly for a resectoscope of claim 1, wherein the cutting electrode loop distal tip is smaller than the coagulation electrode loop distal tip.

3. The electrode assembly for a resectoscope of claim 2, further comprising:
   insulation surrounding at least a portion of the cutting electrode and the coagulation electrode.

4. A resectoscope, comprising:
   a sheath including a sheath lumen, a distal end and a proximal end;
   an electrode assembly positioned in the sheath assembly and including,
   a cutting electrode with a distal tip loop geometry;
   a coagulation electrode with a distal tip loop geometry in fixed physical relationship with the cutting electrode loop distal tip, the cutting electrode distal tip loop and the coagulation electrode distal tip loop being energizable for simultaneously cutting and coagulating tissue;
   a working element attached to the proximal end of the sheath;
   a visualization apparatus housed in a lumen extending from the sheath distal end to a proximal end of the working element, and
   means for splitting and supplying energy from an energy source to both the cutting and coagulation electrodes, wherein the coagulation electrode provides tissue coagulation simultaneously while the cutting electrode cuts tissue.

5. The resectoscope of claim 4, wherein the electrode assembly is slidably positioned in the sheath lumen.

6. The resectoscope of claim 4, further comprising:
   a handle including a thumb grip and a finger grip functioning as an electrode assembly advancement device to advance the cutting electrode distal end and the coagulation electrode distal end in and out of the distal end of the sheath lumen.

7. The resectoscope of claim 4, wherein the cutting electrode can be a coagulation electrode, and the coagulation electrode can be a cutting electrode by selective energization thereof.

8. The resectoscope of claim 4, wherein the cutting electrode distal end is positioned closer to the sheath proximal end than the coagulation electrode distal end.

9. The resectoscope of claim 4, wherein the cutting electrode distal tip and the coagulation electrode distal tip are separated by a distance of 0.25 mm to 10 mm.

10. The resectoscope of claim 4, wherein the cutting electrode distal tip and the coagulation electrode distal tip are separated by a distance of 0.25 mm to 6 mm.

11. The resectoscope of claim 4, wherein the cutting electrode distal tip and the coagulation electrode distal tip are separated by a distance of 0.25 mm to 3 mm.

12. The resectoscope of claim 4, wherein the cutting electrode distal end and the coagulation electrode distal tip are separated by a distance of 3 mm or less.

13. The resectoscope of claim 4, wherein a distance separating the cutting electrode distal end and the coagulation electrode distal end is variable.

14. The resectoscope of claim 4, wherein the cutting electrode distal end and the coagulation electrode distal end are in a fixed relationship to each other.

15. The resectoscope of claim 4, wherein the visualization apparatus is a telescope assembly with optics.

16. The resectoscope of claim 10, wherein the telescope assembly includes a fiber optic.

17. The resectoscope of claim 4, wherein a proximal end of the visualization apparatus includes a magnification eyepiece.

18. The resectoscope of claim 4 wherein the cutting and coagulation electrodes having a parallel pair of arms, and further comprising:
   a spacing sleeve disposed between the visualization apparatus and the parallel pair of arms of the cutting and coagulation electrodes.

19. The resectoscope of claim 4, wherein the electrode assembly operates in a bipolar mode.

20. The resectoscope of claim 4, wherein the electrode assembly operates in a monopolar mode.

* * * * *